(12) United States Patent
Hong

(10) Patent No.: US 8,273,757 B2
(45) Date of Patent: Sep. 25, 2012

(54) COMBINATION OF TWO ANALGESIC CHEMICALS

(76) Inventor: Yanguo Hong, Fujian (CN)

( * ) Notice: Subject to any disclaimer, the term of this patent is extended or adjusted under 35 U.S.C. 154(b) by 276 days.

(21) Appl. No.: 12/871,268

(22) Filed: Aug. 30, 2010

(65) Prior Publication Data

US 2011/0136839 A1 Jun. 9, 2011

(30) Foreign Application Priority Data

Dec. 5, 2009 (CN) .......................... 2009 1 0260428

(51) Int. Cl.
*A01N 43/54* (2006.01)
*A01N 31/14* (2006.01)
*A01N 31/08* (2006.01)
*A01N 27/00* (2006.01)
*A61K 31/517* (2006.01)
*A61K 31/75* (2006.01)
*A61K 31/05* (2006.01)
*A61K 31/15* (2006.01)

(52) U.S. Cl. ................... 514/266.22; 514/721; 514/736; 514/765

(58) Field of Classification Search ............. 514/266.22, 514/721, 736, 765
See application file for complete search history.

(56) References Cited

PUBLICATIONS

Hadengue et al. "Combination of Ketanserin and Verapamil or Proranolol in Patients with Alcoholic Cirrhosis: Search for an Additive Effect" Heptology, 1989, vol. 9, No. 1, pp. 83-87.*
Okin et al. "Serotonergic Blockade Compared with Beta-Adrenergic Blockade in Systemic Hypertension: A Double-Blind Comparison of Ketanserin with Propranolol" J Clin Pharmacol, 1988, vol. 28, pp. 1008-1016.*
Williams et al. "Pharmacodynamics and pharmacokinetics of single doses of ketanserin and propranolol alone and in combination in healthy volunteers" Br. J. clin. Pharmac, 1986, vol. 22, pp. 301-308.*
Rowley DAaBEP (1956) 5-Hydroxytryptamine and histamine as mediators of the vascular injury produced by agents which damage mast cells in rats. J Exp Med 103:399-412.
Sawynok J, Zarrindast MR, Reid AR, Doak GJ (1997) Adenosine A3 receptor activation produces nociceptive behaviour and edema by release of histamine and 5-hydroxytryptamine. Eur J Pharmacol 333:1-7.
Schaible HG, Schmidt RF (1985) Effects of an experimental arthritis on the sensory properties of fine articular afferent units. J Neurophysiol 54:1109-1122.
Schmelz M, Schmidt R, Weidner C, Hilliges M, Torebjork HE, Handwerker HO (2003) Chemical response pattern of different classes of C-nociceptors to pruritogens and algogens. J Neurophysiol 89:2441-2448.
Sicuteri F, Franciullacci M, Franchi G, Delbianco PL (1965a) Serotonin—bradykinin potentiation of the pain receptors in man. Life Sci 35:309-316.
Sluka KA (1998) Blockade of N- and P/Q-type calcium channels reduces the secondary heat hyperalgesia induced by acute inflammation. J Pharmacol Exp Ther 287:232-237.
Sluka KA, Bailey K, Bogush J, Olson R, Ricketts A (1998a) Treatment with either high or low frequency TENS reduces the secondary hyperalgesia observed after injection of kaolin and carrageenan into the knee joint. Pain 77:97-102.
Yaksh TL (1997) Pharmacology and mechanisms of opioid analgesic activity. Acta Anaesthesiol Scand 41:94-111.
Yu YC, Koo ST, Kim CH, Lyu Y, Grady JJ, Chung JM (2002) Two variables that can be used as pain indices in experimental animal models of arthritis. J Neurosci Methods 115:107-113.
Zhang L, Lu Y, Chen Y, Westlund KN (2002) Group I metabotropic glutamate receptor antagonists block secondary thermal hyperalgesia in rats with knee joint inflammation. J Pharmacol Exp Ther 300:149-156.
Carlton SM (2001) Peripheral excitatory amino acids. Curr Opin Pharmacol 1:52-56.
Coderre TJ, Wall PD (1988) Ankle joint urate arthritis in rats provides a useful tool for the evaluation of analgesic and anti-arthritic agents. Pharmacol Biochem Behav 29:461-466.
Di Rosa M, Giroud JP, Willoughby DA (1971) Studies on the mediators of the acute inflammatory response induced in rats in different sites by carrageenan and turpentine. J Pathol 104:15-29.
Doi-Saika M, Tokunaga A, Senba E (1997) Intradermal 5-HT induces Fos expression in rat dorsal horn neurons not via 5-HT3 but via 5-HT2A receptors. Neurosci Res 29:143-149.
Foon KA, Wahl SM, Oppenheim JJ, Rosenstreich DL (1976) Serotonin-induced production of a monocyte chemotactic factor by human peripheral blood leukocytes. J Immunol 117:1545-1552.
Abbott FV, Hong Y, Blier P (1996) Activation of 5-HT2A receptors potentiates pain produced by inflammatory mediators. Neuropharmacology 35:99-110.
Abbott FV, Hong Y, Blier P (1997) Persisting sensitization of the behavioural response to formalin-induced injury in the rat through activation of serotonin2A receptors. Neuroscience 77:575-584.
Armstrong D, Dry RM, Keele CA, Markham JW (1953) Observations on chemical excitants of cutaneous pain in man. J Physiol 120:326-351.
Babenko V, Graven-Nielsen T, Svensson P, Drewes AM, Jensen TS, Arendt-Nielsen L (1999) Experimental human muscle pain and muscular hyperalgesia induced by combinations of serotonin and bradykinin. Pain 82:1-8.
Beck PW, Handwerker HO (1974) Bradykinin and serotonin effects on various types of cutaneous nerve fibers. Pflugers Arch 347:209-222.

(Continued)

*Primary Examiner* — Sreeni Padmanabhan
*Assistant Examiner* — Kendra D Carter

(57) ABSTRACT

The present invention is a novel analgesic combination and its use. It is classified to be an invention in the field of medicine and technology. The purpose of this invention is to solve the problem that existing analgesics does not effectively attenuate pain or produces serious side-effects in clinic. The ingredients of the analgesic combination include ketanserin and propranolol. This combination is used to make a drug to treat pain. Because the ingredients of the analgesic combination target peripheral receptors, the unwanted effects could be only minimal. The big advantage of this combination is that each of the ingredients acts on the different receptors producing the synergizing analgesic. Therefore, the analgesia that the combination produces is remarkable and the effective doses are low.

2 Claims, 8 Drawing Sheets

PUBLICATIONS

Bleehen T, Keele CA (1977) Observations on the algogenic actions of adenosine compounds on the human blister base preparation. Pain 3:367-377.

Cardenas LM, Cardenas CG, Scroggs RS (2001) 5HT increases excitability of nociceptor-like rat dorsal root ganglion neurons via cAMP-coupled TTX-resistant Na(+) channels. J Neurophysiol 86:241-248.

Francischi JN, Chaves CT, Moura AC, Lima AS, Rocha OA, Ferreira-Alves DL, Bakhle YS (2002) Selective inhibitors of cyclo-oxygenase-2 (COX-2) induce hypoalgesia in a rat paw model of inflammation. Br J Pharmacol 137:837-844.

Grubb BD, McQueen DS, Iggo A, Birrell GJ, Dutia MB (1988b) A study of 5-HT-receptors associated with afferent nerves located in normal and inflamed rat ankle joints. Agents Actions 25:216-218.

Herbert MK, Schmidt RF (1992) Activation of normal and inflamed fine articular afferent units by serotonin. Pain 50:79-88.

Holsapple MP, Schnur M, Yim GK (1980) Pharmacological modulation of edema mediated by prostaglandin, serotonin and histamine. Agents Actions 10:368-373.

Hong Y, Abbott FV (1994) Behavioural effects of intraplantar injection of inflammatory mediators in the rat. Neuroscience 63:827-836.

Hong Y, Abbott FV (1995) Peripheral opioid modulation of pain and inflammation in the formalin test. Eur J Pharmacol 277:21-28.

Horigome K, Pryor JC, Bullock ED, Johnson EM, Jr. (1993) Mediator release from mast cells by nerve growth factor. Neurotrophin specificity and receptor mediation. J Biol Chem 268:14881-14887.

Houghton AK, Lu Y, Westlund KN (1998) S-(+)-3-isobutylgaba and its stereoisomer reduces the amount of inflammation and hyperalgesia in an acute arthritis model in the rat. J Pharmacol Exp Ther 285:533-538.

Ito S, Okuda-Ashitaka E, Minami T (2001) Central and peripheral roles of prostaglandins in pain and their interactions with novel neuropeptides nociceptin and nocistatin. Neurosci Res 41:299-332.

Jensen K, Tuxen C, Pedersen-Bjergaard U, Jansen I, Edvinsson L, Olesen J (1990c) Pain and tenderness in human temporal muscle induced by bradykinin and 5-hydroxytryptamine. Peptides 11:1127-1132.

Jensen K, Tuxen C, Pedersen-Bjergaard U, Jansen I, Edvinsson L, Olesen J (1990d) Pain, wheal and flare in human forearm skin induced by bradykinin and 5-hydroxytryptamine. Peptides 11:1133-1138.

Jiang J, Huang J, Hong Y (2006) Bovine adrenal medulla 22 reverses antinociceptive morphine tolerance in the rat. Behav Brain Res 168:167-171.

Tokunaga A, Saika M, Senba E (1998) 5-HT2A receptor subtype is involved in the thermal hyperalgesic mechanism of serotonin in the periphery. Pain 76:349-355.

Tramontana M, Giuliani S, Del Bianco E, Lecci A, Maggi CA, Evangelista S, Geppetti P (1993) Effects of capsaicin and 5-HT3 antagonists on 5-hydroxytryptamine-evoked release of calcitonin gene-related peptide in the guinea-pig heart. Br J Pharmacol 108:431-435.

Vinegar R, Truax JF, Selph JL, Johnston PR (1989) Pharmacological characterization of the algesic response to the subplantar injection of serotonin in the rat. Eur J Pharmacol 164:497-505.

Wei H, Chen Y, Hong Y (2005) The contribution of peripheral 5-hydroxytryptamine2A receptor to carrageenan-evoked hyperalgesia, inflammation and spinal Fos protein expression in the rat. Neuroscience 132:1073-1082.

Williams S, Evan GI, Hunt SP (1990) Changing patterns of c-fos induction in spinal neurons following thermal cutaneous stimulation in the rat. Neuroscience 36:73-81.

Wisden W, Errington ML, Williams S, Dunnett SB, Waters C, Hitchcock D, Evan G, Bliss TV, Hunt SP (1990) Differential expression of immediate early genes in the hippocampus and spinal cord. Neuron 4:603-614.

Parada CA, Tambeli CH, Cunha FQ, Ferreira SH (2001) The major role of peripheral release of histamine and 5-hydroxytryptamine in formalin-induced nociception. Neuroscience 102:937-944.

Pertsch M, Krause E, Hirschelmann R (1993) A comparison of serotonin (5-HT) blood levels and activity of 5-HT2 antagonists in adjuvant arthritic Lewis and Wistar rats. Agents Actions 38 Spec No. C98-101.

Pierce PA, Xie GX, Peroutka SJ, Green PG, Levine JD (1995) 5-Hydroxytryptamine-induced synovial plasma extravasation is mediated via 5-hydroxytryptamine2A receptors on sympathetic efferent terminals. J Pharmacol Exp Ther 275:502-508.

Pozo MA, Balazs EA, Belmonte C (1997) Reduction of sensory responses to passive movements of inflamed knee joints by hylan, a hyaluronan derivative. Exp Brain Res 116:3-9.

Radhakrishnan R, Moore SA, Sluka KA (2003) Unilateral carrageenan injection into muscle or joint induces chronic bilateral hyperalgesia in rats. Pain 104:567-577.

Rang HP, Bevan S, Dray A (1991) Chemical activation of nociceptive peripheral neurones. Br Med Bull 47:534-548.

Richardson BP, Engel G, Donatsch P, Stadler PA (1985) Identification of serotonin M-receptor subtypes and their specific blockade by a new class of drugs. Nature 316:126-131.

Khalil Z, Helme RD (1990a) Serotonin modulates substance P-induced plasma extravasation and vasodilatation in rat skin by an action through capsaicin-sensitive primary afferent nerves. Brain Res 527:292-298.

Kim SH, Chung JM (1992) An experimental model for peripheral neuropathy produced by segmental spinal nerve ligation in the rat. Pain 50:355-363.

Lewin GR, Rueff A, Mendell LM (1994) Peripheral and central mechanisms of NGF-induced hyperalgesia. Eur J Neurosci 6:1903-1912.

Neugebauer V (2001) Peripheral metabotropic glutamate receptors: fight the pain where it hurts. Trends Neurosci 24:550-552.

Okamoto K, Imbe H, Morikawa Y, Itoh M, Sekimoto M, Nemoto K, Senba E (2002) 5-HT2A receptor subtype in the peripheral branch of sensory fibers is involved in the potentiation of inflammatory pain in rats. Pain 99:133-143.

Orwin JM, Fozard JR (1986) Blockade of the flare response to intradermal 5-hydroxytryptamine in man by MDL 72.222, a selective antagonist at neuronal 5-hydroxytryptamine receptors. Eur J Clin Pharmacol 30:209-212.

Palmer SL, Thakur GA, Makriyannis A (2002) Cannabinergic ligands. Chem Phys Lipids 121:3-19.

* cited by examiner

COMBINATION OF TWO ANALGESIC CHEMICALS

BACKGROUND OF THE INVENTION

Pain is a protective mechanism warning that the body needs medical help. Actually at least half of patients see doctors because they suffer from pain. However, chronic pain does not display protective significance but seriously bothers people's life. Existing analgesics either are not very effective or produce serious adverse effects, or both. For example, opioids induce constipation and inhibit respiration. There is also an abuse potential with opiates, and the fear of dependence reduces compliance for this class of drugs. The COX-2 inhibitors family has been plagued by a number of adverse effects, some of which are even lethal. The old stand-by NSAIDs are also plagued by lethal serious adverse effects. Therefore, there is a competitive advantage in developing a drug that targets peripheral receptors because it would lacks CNS adverse effects.

It has been documented that many receptors in the periphery are involved in induction or modulation of pain, such as opioid (Hong & Abbott, 1995;Yaksh, 1997), glutamate (Carlton, 2001;Neugebauer, 2001), CB1 and CB2 (Palmer et al., 2002), prostaglandin (Francischi et al., 2002;Ito et al., 2001) etc. Activation or inhibition of these receptors suppresses pain, indicating that it is feasible to target peripheral receptors to relieve pain.

Inflammatory and injured pain is induced following the activation of primary sensory neurons. It is a variety of chemical mediators released during inflammation that maintains activity of primary afferents and/or enhances nociceptor sensitivity leading to hyperalgesia or allodynia. 5-HT (5-hydroxytryptamine or serotonin) is one of inflammatory mediators (Foon et al., 1976), playing a key role in the development of pain (Hong & Abbott, 1994). This chemical is released from platelets, mast cells and endothelial cells into a wound site after tissue injury and inflammation (Parada et al., 2001; Rowley, 1956). 5-HT activates c-fiber afferents (Beck & Handwerker, 1974;Herbert & Schmidt, 1992;Grubb et al., 1988), increases excitability of small-diameter neurons in the dorsal root ganglia (Cardenas et al., 2001) and release CGRP (Tramontana et al., 1993), indicating that it is a pro-algesic or nociceptive agent. 5-HT itself is involved in the induction of pain as application of 5-HT to the blister base or skin in humans causes pain sensation (Jensen et al., 1990a; Jensen et al., 1990b;Armstrong et al., 1953;Richardson et al., 1985; Orwin & Fozard, 1986). It has been documented that the high plasma 5-HT level is associated with adjuvant arthritis. (Pertsch et al., 1993). 5-HT can be ascribed for NGF-induced inflammation and hyperalgesia as NGF causes degranulation of mast cells and releases 5-HT (Horigome et al., 1993;Lewin et al., 1994). Furthermore, 5-HT sensitizes nociceptive responses evoked by mechanical, thermal and chemical stimuli, inducing pain (Vinegar et al., 1989;Rang et al., 1991; Hong & Abbott, 1994;Schmelz et al., 2003) or potentiating pain produced by other inflammatory mediators, such as substance P. noradrenaline. prostaglandin E2, bradykinin, etc. in animals (Hong & Abbott, 1994;Khalil & Helme, 1990) and humans (Jensen et al., 1990a;Jensen et al., 1990b; Sicuteri et al., 1965;Bleehen & Keele, 1977;Babenko et al., 1999). These may underlie the key role of 5-HT in pain associated with tissue injury and inflammation (Holsapple et al., 1980; Hong & Abbott, 1994;Di Rosa et al., 1971;Khalil & Helme, 1990).

5-HT interacts with multiple subtypes of 5-HT receptors in the periphery to produce nociception, among which 5-HT2A receptor is pivotal. This notion is based on the facts that serotonin-induced hyperalgesia and enhancement on pain produced by noradrenaline and prostaglandin E2 are mimicked by 5-HT2A receptor agonists, but not by the agents acting at 5-HT1A and 5-HT3 receptors. Correspondingly, nociceptive response induced by serotonin is specifically abolished by 5-HT2A receptor antagonist, but not by the blockade of 5-HT1A and 5-HT3 receptors. (Grubb et al., 1988;Abbott et al., 1996;Doi-Saika et al., 1997;Tokunaga et al., 1998). 5-HT2A receptor antagonist, ketanserin, also profoundly suppresses serotonin-induced plasma extravasation in the knee joint model of inflammation as well (Pierce et al., 1995). Particularly, the mediation of 5-HT2A receptor in pain has been demonstrated in the widely used pain models, such as formalin test (Abbott et al., 1997), CFA (Okamoto et al., 2002) and carrageenan (Wei et al., 2005) models of inflammation and arthritis (Pertsch et al. 1993). In addition, 5-HT2A receptor is involved in the development of hyperalgesia and edema induced by the nociceptive mediator adenosine (Sawynok et al., 1997).

As inflammatory site is actually a source for the development and maintenance of pain, pain may be relieved by targeting the $5\text{-HT}_{2A}$ receptor in this local site. This can be achieved by local or systemic injection of $5\text{-HT}_{2A}$ antagonists. More importantly, we have found that combination of two compounds that target two different receptors produces synergistic antinociception. Our results have demonstrated that targeting two receptors has produced a significant inhibition on nociceptive responses in animal studies. This analgesic drug targets two novel targets. Either of the compounds selectively targets their respective receptor and produces potent analgesic in inflammatory pain with rapid onset and lack of adverse effects. Each drug produces a naloxone-reversible hypoalgesia suggesting the activation of an endogenous opioid mechanism. Interestingly, when the two compounds are administered together, lower doses of each compound can elicit the significant antinociceptive effects. Moreover, both local and systemic injections of the combination are equally effective. The combination also did not induce overt adverse effects or tolerance to the drugs. Furthermore, the combination is effective in relieving neuropathic pain which is not even responsive to opioids sometimes. Preclinical tests have been completed and potential applications of this combination include arthritis, muscleskeletal pain syndrome, general inflammatory pain and neuropathic pain. The results that were obtained in this laboratory are summarized below. It should he addressed that our goal was to develop good analgesic without site effects. This new drug does not have to be better than morphine for inhibition of nociception. Therefore, the comparison with morphine or other powerful existing analgesic has not been designed.

SUMMARY OF THE INVENTION

The present invention is about a combination of two chemicals that shows a novel use. It has solved the problem that available analgesics display either less potency or remarkable side-effects. This combination targets peripheral receptors and produces satisfied antinociception with unnoticeable side-effects. Ingredients in the combination act on the different receptors. However, their combined use exerts a synergistic action. It produces remarkable analgesia. In addition, the effective dose of drugs is low.

Both drugs and the combination have never been realized or used to treat pain.

The ingredients of the analgesia combination are ketanserin and propranolol. This combination is used to treat pain.

The excellence of the present invention:

One of the ingredients exerts synergistic action with the other one. The combination blocks two different receptors. Antagonism against these two receptors displays synergistic action. This novel combination acts on the two targets which have never been targeted for the sake of analgesia. It should be addressed that the two drugs in the mixture is delivered at the same time with smaller dose than that when it is given alone. Moreover, local delivery of the drugs produces the same effect as systemic injection. In addition, the onset of the action is fast and the combination does not induce side-effects or tolerance.

Mechanism of the present invention: Ketanserin and propranolol are selective 5-HT2A and 5-HT1A receptor antagonist, respectively. Each of them antagonizes its own receptors and exerts remarkable analgesia. Furthermore, both drugs can induce hypoalgesia and this response is reversed by naloxone suggesting an endogenous opioid mechanism.

In the clinic, ketanserin is used as an adjuvant for the treatment of hypertension while propranolol is used to reduce heart rate. Our animal study has shown that subcutaneous injection of ketanserin or propranolol at 0.5 mg/kg does not alter the blood pressure and heart rate. This is in agreement with the established conclusions that ketanserin does not reduce blood pressure in humans with a normal pressure and that propranolol displays moderate action t and does not produce position-associated hypotension. Importantly, the effective dose of the each drug in the combination is 5-10 times lower than the usual usage. Therefore, the side-effects are not noticeable. The combination does not increase the adverse effects or produce new deleterious effects.

DETAILED DESCRIPTION OF THE INVENTION

Ingredients of the present invention of the analgesic combination chemicals are (percentage of weight):

Ketanserin: 50-70%

Propranolol: 50-30%

The two ingredients ketanserin and propranolol should be evenly mixed according to the above proportions to get the analgesic combination.

The ingredients ketanserin and propranolol in the combination arc available in the market.

The combination is a drug that is made to treat pain. The powders in combination of the present invention are dissolved in injected vehicle to make injected drug. The components of this combination are dissolved in injected water to make injected drug which contains 1-50 mg of combination in 1 ml injected water.

The use of the invention analgesia combination is to treat arthritic pain, muscleskeletal pain syndrome, general inflammatory pain and neuropathic pain. The ingredients prescribed in this combination are mixed according to the defined proportions and dissolved in the injected water (1-50 mg drugs, in 1 ml water). Then the mixed combination can be injected subcutaneously. The effective dose is 0.05-0.5 mg/kg, once or twice per day for 7-14 days depending on the severity of pain. However, period of treatment can be shorter or longer depending on the effect.

Exemplification

EXAMPLE 1

Effects of Local Injection of 5-HT Antagonists

Carrageenan Model and Pain Sensitivity Assessment

Rats received a subcutaneous injection of carrageenan (2% in saline, 100 µl) in the right hindpaw (intraplantar injection). Drug or vehicle were administered intraplantarly (i.pl., 50 µl) 1 hour after carrageenan injection and behavioral testing was performed at various time points. Nociceptive threshold responding to heat was determined as described before (Williams et al., 1990;Wisden et al., 1990:Jiang et al., 2006). Briefly, rat was placed in a device that held the body without restraining the head and legs. Noxious heat stimulation was carried out by immersing the hindpaw up to the ankle joint into a slowly stirred water bath at 47.5° C. while holding the animal with the device. This temperature produced an average baseline PWL (paw withdrawal latency) of 7-10 s in naive paw. Paw withdrawal latency for any test time point was measured twice at 3-min intervals and the mean values were calculated. Baseline latency was measured 10 min before drug or vehicle administration.

Result I-1 Effects of intraplantar injection of ketanserin on thermal hyperalgesia (paw withdraw test).

Figure 1:
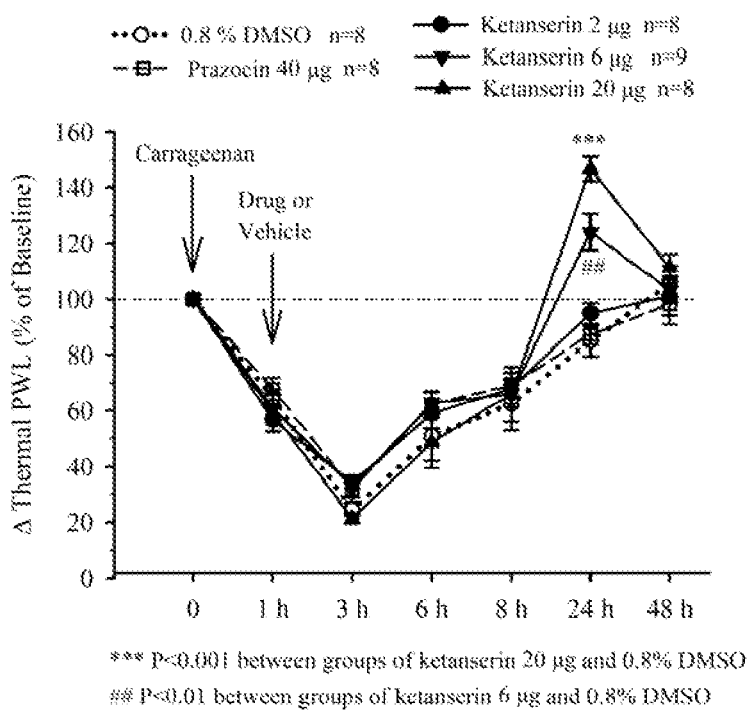
FIG. 1 shows the effects of ketanserin on inflammatory hyperalgesia.

Effects of ketanserin on carrageenan-evoked hyperalgesia are illustrated in FIG. 1. Paw withdrawal latencies in seconds were measured in plantar test at the various time points. Data were normalized as percentage of pretreatment baseline (100%) and expressed as the mean±SEM (standard error of mean). Carrageenan (2%, 100 µl was administered i.pl. in one hindpaw at 0 hour and 0.8% DMSO (50 µl, i.pl.) or ketanserin (2, 6 and 20 µg in 50 µl, i.pl.) or prazosin (40 µg, i.pl.) at 1 hour. *** represents P<0.001 compared with control (carrageenan/0.8% DMSO). The means of PWLs before injection of carrageenan were 6.6-7.9 sec.

Summary: Local injection of the 5-HT$_{2A}$ antagonist ketanserin in the inflamed paw dose-dependently produces hypoalgesia in the inflamed area that displays lower nociceptive threshold than normal. The selective □1-adrenergic receptor antagonist prazosin failed to alter the carrageenan-evoked response suggesting that ketanserin-induced hypoalgesia is specific.

Result I-2 Reversal of ketanserin-induced hyporalgesia by naloxone

Figure 2:
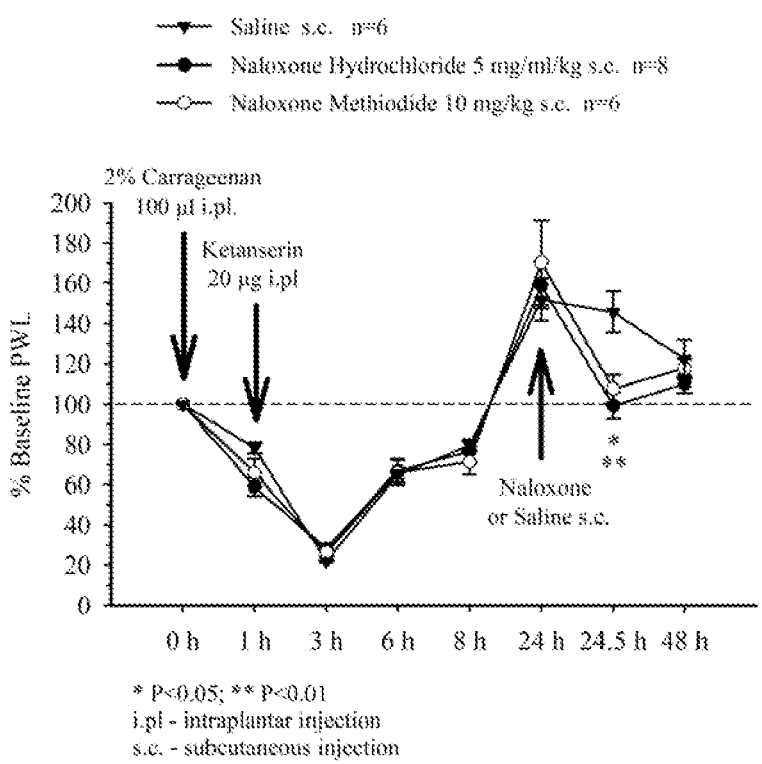
FIG. 2 shows the reversal of ketanserin-associated hypoalgesia by the opioid receptor antagonist naloxone.

Reversal of ketanserin-associated hypoalgesia in carrageenan-evoked inflammation by opioid receptor antagonist is shown in FIG. 2. Paw withdrawal latencies in seconds were determined in plantar test at the various time points. Data were normalized as percentage of pretreatment baseline (100%) and expressed as the mean±SEM. Carrageenan and ketanserin (20 μg) were given i.pl. into unilateral hindpaw at 0 and 1 hour, respectively. Then naloxone chloride (5 mg/kg) or naloxone methiodide (10 mg/kg) or saline (1 ml/kg) was injected s.c. (subcutaneous injection) at 24 hours after carrageenan. * represents P<0.05 and ** P<0.01 compared with group of carrageenan/ketanserin/saline.

Conclusion: Ketanserin-induced hypoalgesia in the inflamed paw is mediated by opioid analgesia mechanism.

Figure 3:
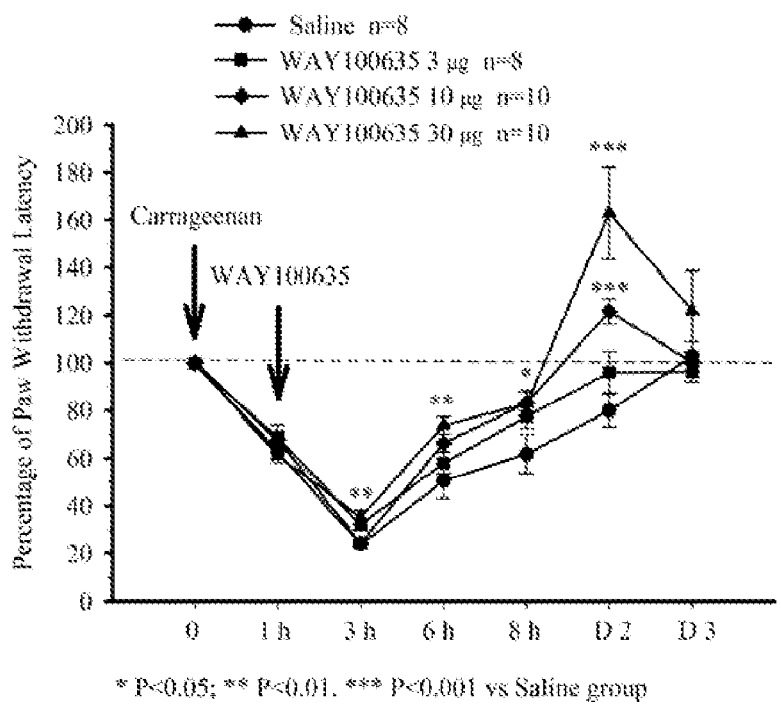
FIG. 3 shows the effects of WAY100635 on inflammatory hyperalgesia.

Result I-3 Effect of intraplantar injection of WAY100635 on thermal hyperalgesia Effect of WAY100635 on carrageenan-evoked response is demonstrated in FIG. 3. Paw withdrawal latencies in seconds were examined at the various time points. Data were normalized as percentage of pretreatment baseline (100%) and expressed as the mean±SEM. (A) Carrageenan (2%, 100 μl) was administered i.pl. at 0 hour and 0.8% DMSO (50 μl, i.pl.) or WAY100635 (3, 10 and 30 μg, i.pl.) at 1 hour. * represents P<0.05,  P<0.01 and * P<0.001 compared with control (carrageenan/DMSO).

Summary: Local injection of the 5-HT$_{1A}$ antagonist WAY10063 in the inflamed paw dose-dependently produces hypoalgesia in the inflamed area that displays lower nociceptive threshold than normal. Nociceptive response is higher but nociceptive threshold is lower.

Figure 4:
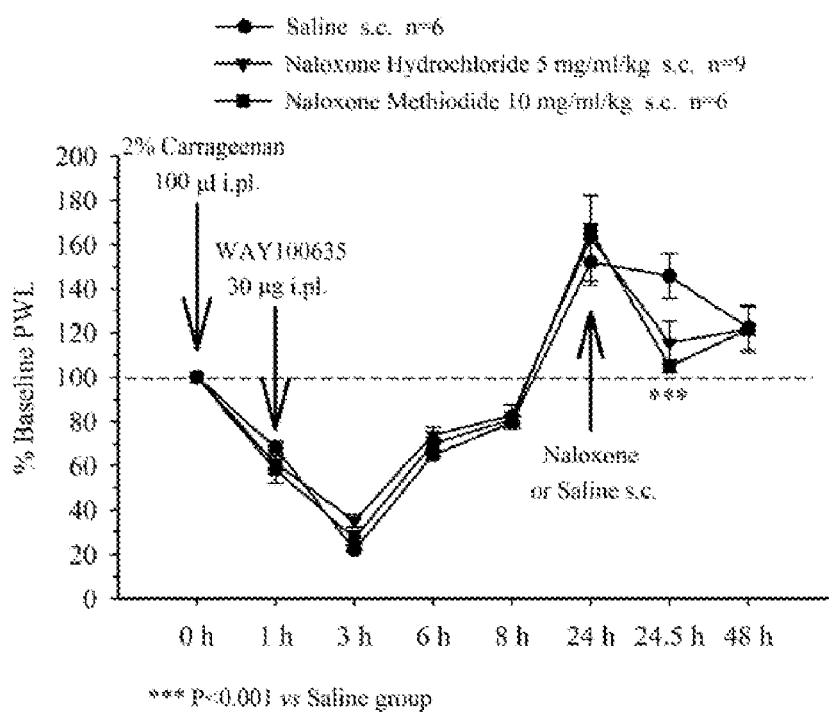
FIG. 4 shows the reversal of WAY100635-associated hypoalgesia by naloxone.

Result I-4 Reversal of WAY1000635-induced hyporalgesia by naloxone (FIG. 4)

Carrageenan and WAY100365 (30 μg) were given i.pl. into unilateral hindpaw at 0 and 1 hour, respectively. Then naloxone chloride (5 mg/ml/kg) or naloxone methiodide (10 mg/ml/kg) or saline (1 ml/kg) was injected s.c. (subcutaneous injection) at 24 hours after carrageenan. Paw withdrawal latencies in seconds were measured at the various time points. Data were normalized as percentage of pretreatment baseline (100%) and expressed as the mean±SEM. *** represents P<0.001 compared with group of carrageenan/WAY100365/saline.

Conclusion: WAY100365-induced hypoalgesia in the inflamed paw is mediated by opioid analgesia mechanism.

Figure 5:
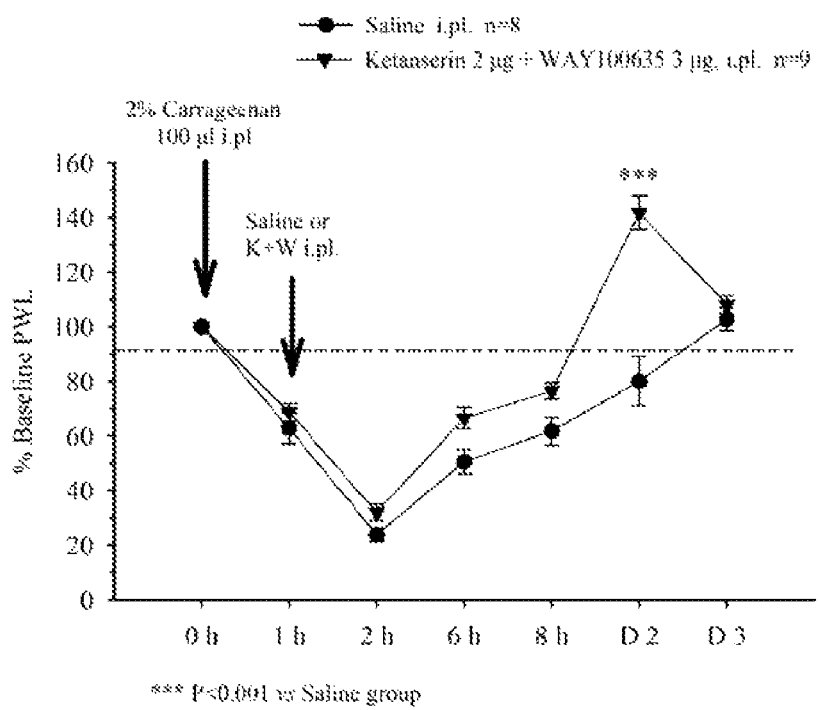
FIG. 5 shows the effect of local injection of ketanserin and WAY100635 on inflammatory hyperalgesia.

Result I-5 Enhancement effect of a combination of ketanserin+WAY1000635 (FIG. 5)

Carrageenan (2%, 100 μl) was administered i.pl. at 0 hour and saline (50 μl, i.pl.) or ketanserin (2 μg, i.pl.)+WAY100635 (3 μg, i.pl.) at 1 hour. The results are illustrated in FIG. 5. Paw withdrawal latencies in seconds were examined at the various time points. Data were normalized as percentage of pretreatment baseline (100%) and expressed as the mean±SEM. *** represents P<0.001 compared with control (carrageenan/saline).

Summary: Local injection of ketanserin plus WAY10063 with ineffective doses produces significant inhibition on hyperalgesia in the inflamed paw.

EXAMPLE 2

Effects of Systemic Injection of a Combination

Methods

Carrageenan model—See those described before.

Arthritis model—Arthritis was induced using a modification of the previously described method (Schaible & Schmidt, 1985; Pozo et al., 1997; Sluka, 1998; Zhang et al., 2002). Briefly, rat was anesthetized with barbiturate (Nembutal; 45 mg/kg). A solution of kaolin (4% in distilled water, 0.1 ml) was injected into the synovial cavity of right knee joint. Then, the knee joint was flexed and extended within the normal range of motion at regular intervals for 15 min. After that, 0.1 ml of a 2% aqueous solution of carrageenan (in saline) was injected into the joint cavity. The knee joint was again manipulated by slightly rapid flexion and extension movements for 5 min.

Behavioral Test

Behavioral test was conducted before and after induction of arthritis by measuring paw withdrawal latency (PWL). A decrease in the PWL to noxious radiant heat in an animal with knee joint inflammation is indicative of secondary hyperalgesia and is used to assess arthritis (Coderre & Wall, 1988; Houghton et al., 1998; Sluka et al., 1998; Zhang et al., 2002). Thermal hyperalgesia was evaluated by using an analgesimeter (Plantar Test, Ugo Basile, Comerio-Varese, Italy). On the testing day, each animal was placed in a plastic cage with a glass floor. After a 30 min habituation period, the plantar surface of the hind paw was exposed to a beam of radiant heat through the glass floor. The radiant heat source consisted of an infrared bulb. Bulb intensity was adjusted so that the control latency was 8-10 s. A photoelectric cell detected light reflected from the paw and turned off the lamp when paw movement interrupted the reflected light. The PWL was automatically displayed to the nearest 0.1 s. The cut-off time was 20 s in order to avoid damaging dermal tissue. The average of the three trials with 3-min interval was determined before and 4 hours after the induction of arthritis. Thereafter, the PWL measurement was conducted daily for 2 weeks. The PWL before the injection in each rat served as its own control.

Measurement of the Knee Size

To assess inflammation of the knee joint, the rat was anesthetized briefly with halothane and the circumference of the knee joint was measured using a flexible tape measure (Houghton et al., 1998; Yu et al., 2002; Zhang et al., 2002; Sluka et al., 1998).

Musculoskeletal pain model—The model that is used in the previous study (Radhakrishnan et al., 2003) has been modified in the present study. Rats were given injection of lambda carrageenan (Type IV, 3%, 100 μl, dissolved in sterile saline, Sigma Chemical Company, St. Louis, USA) in the left gastrocnemius muscle belly. Five days later, the same agent was re-injected in the gastrocnemius muscle using an identical injection protocol. PWL responding to heat stimulus ipsilaterally was measured.

Neuropathic pain model—The L5 (L means lumbar) spinal nerve of right side of the rat were tightly ligated (Kim & Chung, 1992). Thermal nociceptive threshold was evaluated by paw withdraw latency using an analgesimeter (Plantar Test, Ugo Basile, Comerio-Varese, Italy). The detail has been described in the section of Carrageenan model.

Mechanical threshold was measured in the hindpaw using an automated von Frey type system (Dynamic plantar Aesthesiometer 37400, Ugo Basile, Italy). Animals were acclimatized to the testing apparatus for 20 min for three days and briefly habituated to the test environment for 10 min on test day to minimize intra- and inter-individual variability of behavioral outcome measures. Rats were placed on a metal mesh surface under a plastic enclosure. The stimulator unit was placed beneath the selected hindpaw with the filament below the plantar surface of the rat. A paw-flick response was elicited by application of an increasing force (measure in grams) using a stainless-steel filament (0.5 mm diameter). When the unit was started, the electrodynamic actuator lifted the filament and exerted a force. The force was increased at a rate of 2.5 g/s until the rat moved its paw. A force of 50 g for 30 s was used as cut off to preclude possible damage to the paw. The force was defined as the mean of two measurements at 2 min-interval. The investigator was blind to the test drug conditions.

Figure 6:
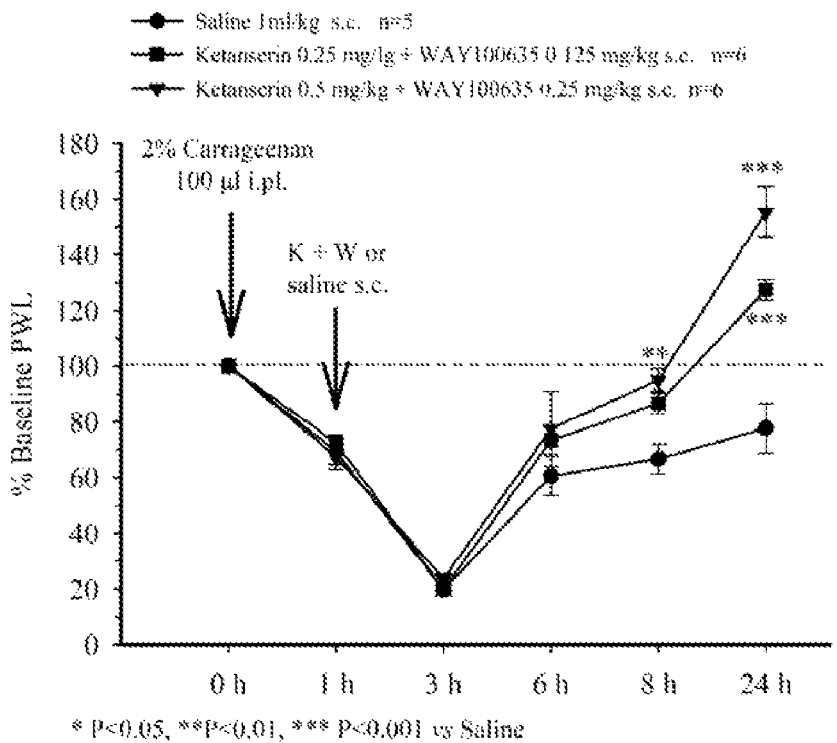
FIG. 6 shows the effects of subcutaneous injection of ketanserin and WAY100635 on inflammatory hyperalgesia.

Result II-1 Effects of subcutaneous injection of a combination (ketanserin+WAY100635) on thermal hyperalgesia in a model of carrageenan-induced inflammation Carrageenan (2%, 100 μl) was administered i.pl. in one hindpaw at 0 hour and saline or ketanserin plus WAY100635 was injected subcutaneously at 1 hour. The results are shown in FIG. 6. Paw withdrawal latency was measured at the various time points. Data were normalized as percentage of pretreatment baseline (100%) and expressed as the mean±SEM. * represents $P<0.05$,  $P<0.01$ and * $P<0.001$ compared with control (carrageenan/saline).

Summary: Systemic injection (subcutaneous) of ketanserin plus WAY10063 raises the nociceptive threshold to higher level than normal.

Result II-2 Dose-dependent effects of subcutaneous injection of ketanserin or propranolol or combination on thermal hyperalgesia in the carrageenan model (FIG. 7).

Figure 7A:
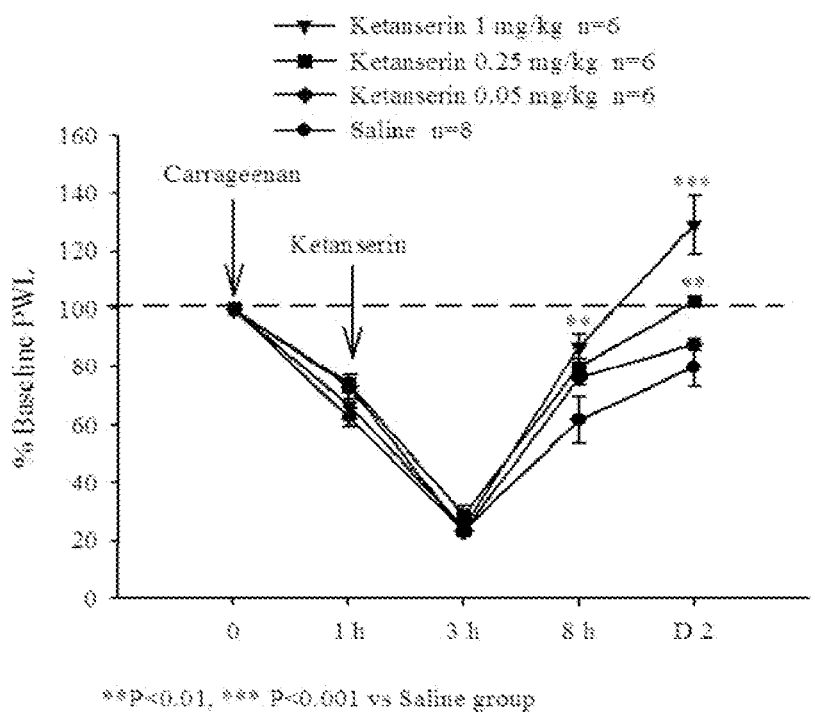
FIG. 7A shows the effect of ketanserin on inflammatory hyperalgesia.
Figure 7B:
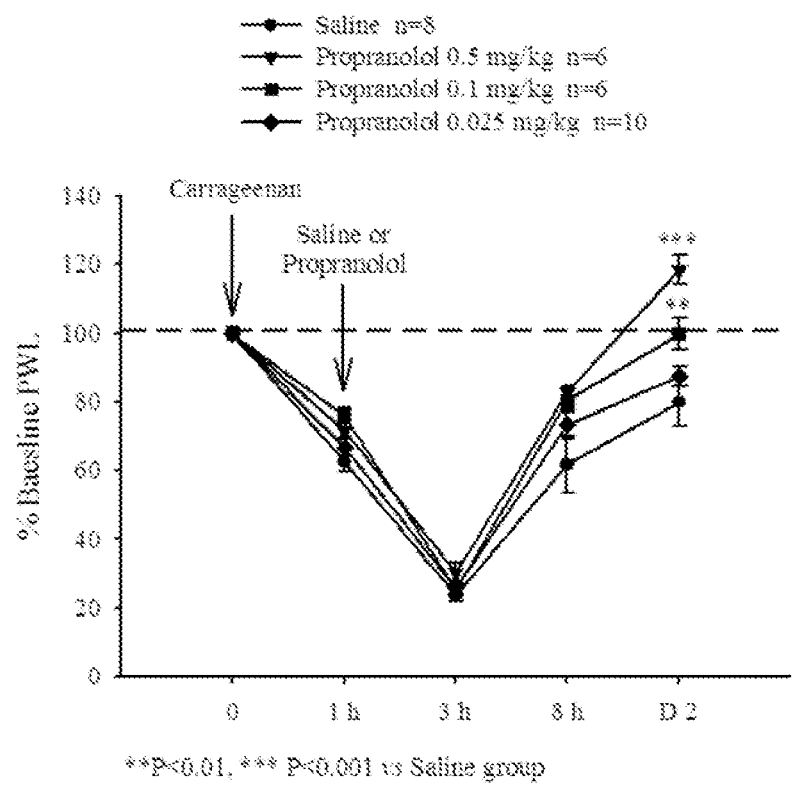
FIG. 7B shows the effect of propranolol on inflammatory hyperalgesia.

Carrageenan (2%, 100 μl) was administered i.pl. in one hindpaw at 0 hour and saline or ketanserin (A) or propranolol (B) was injected subcutaneously at 1 hour in FIG. 7A or FIG. 7B. Paw withdrawal latency was measured at the various time points. Data were normalized as percentage of pretreatment baseline (100%) and expressed as the mean±SEM.  represents $P<0.01$ and * $P<0.001$ compared with control (carrageenan/saline).

Figure 7C:
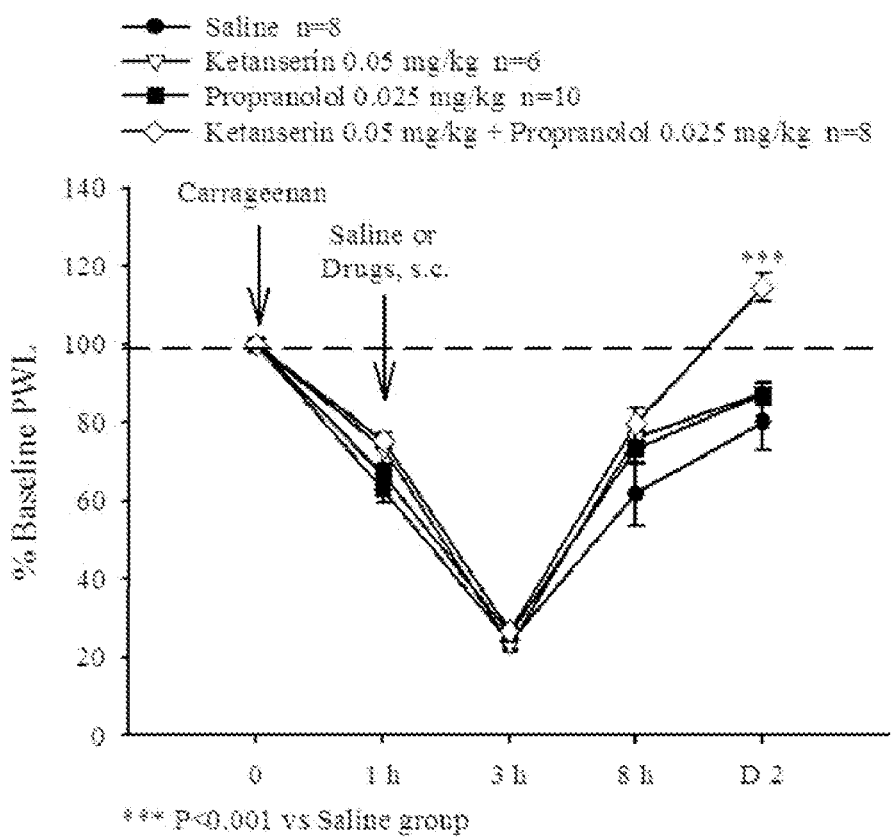
FIG. 7C shows the synergistic effect of ketanserin plus propranolol on inflammatory hyperalgesia.
Figure 7D:
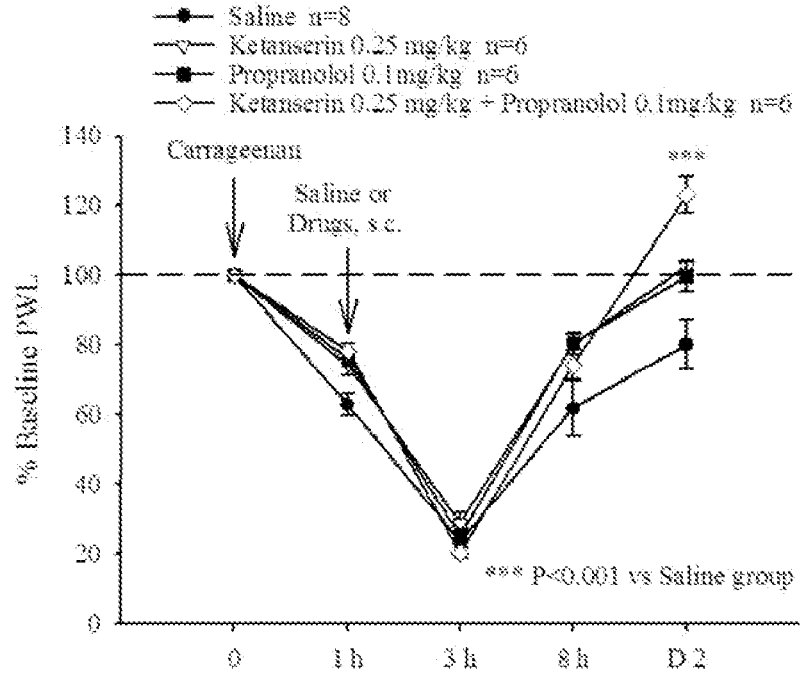
FIG. 7D shows the synergistic effect of ketanserin plus propranolol on inflammatory hyperalgesia.

Carrageenan (2%, 100 μl) was administered i.pl. in one hindpaw at 0 hour and saline or combination (ketanserin plus propranolol) was injected subcutaneously at 1 hour in FIG. 7C or FIG. 7D. Paw withdrawal latency was measured at the various time points. Data were normalized as percentage of pretreatment baseline (100%) and expressed as the mean±SEM. * represents $P<0.05$,  $P<0.01$ and * $P<0.001$ compared with control (carrageenan/saline). FIG. 7C illustrates that combination of ketanserin plus propranolol at low doses exerted synergistic effect which completely inhibited inflammatory hyperalgesia, FIG. 7D illustrates that ketanserin or propranolol alone at higher dose (higher than those in FIG. 7C) exerted stronger effect of on inflammatory hyperalgesia. However, it looks that the combination of these two drugs produced similar synergistic effect compared to FIG. 7C.

Summary: Systemic (subcutaneous) injection of ketanserin or propranolol produces significant inhibition on the nociceptive threshold in the inflamed paw. Injection of lower doses of ketanserin plus propranolol also produces the same effects.

Result II-3 Effects of subcutaneous combination on pain and edema in arthritis model (FIG. 8)

Figure 8A:
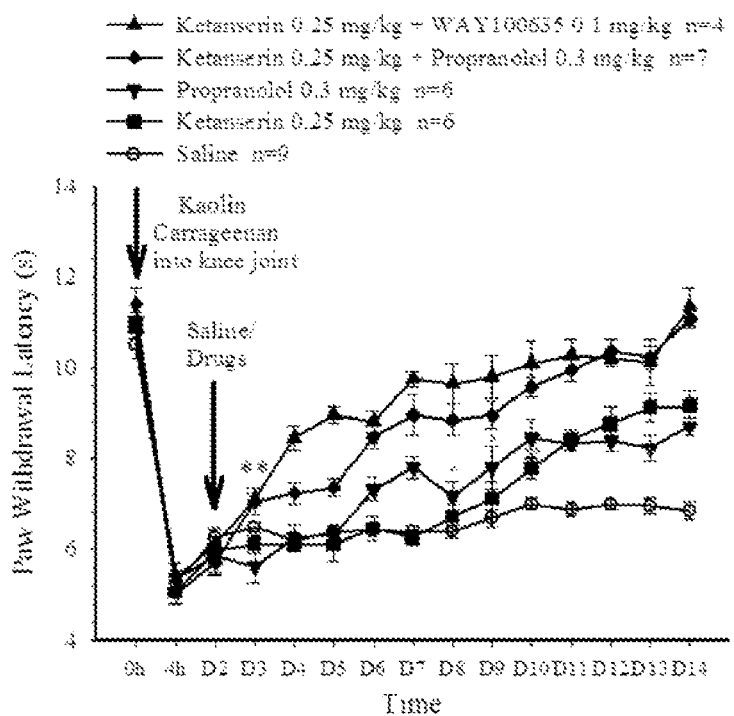
FIG. 8A shows the effects of combination of ketanserin plus propranolol on arthritic pain.
Figure 8B:
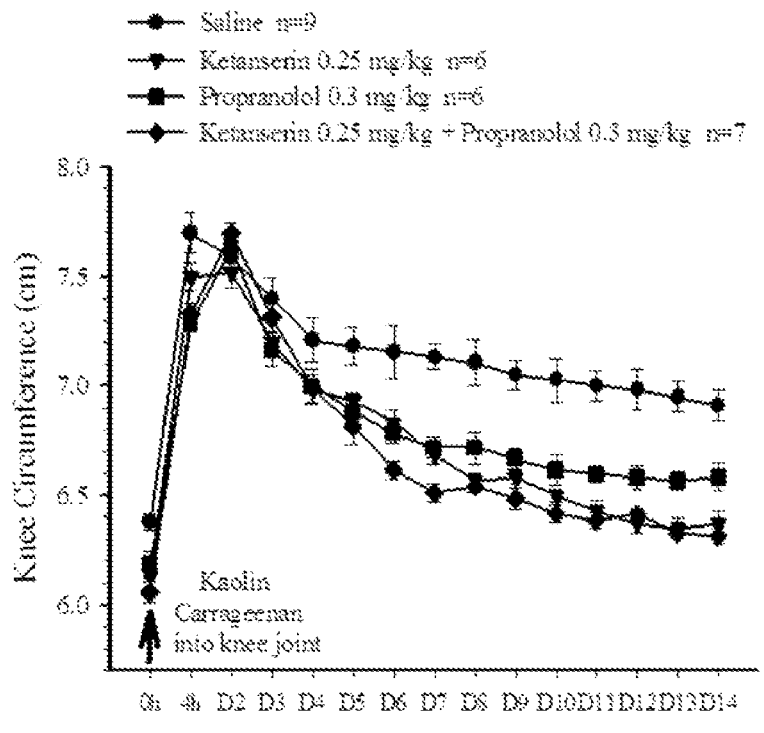
FIG. 8B shows the effects of combination of ketanserin plus propranolol on arthritic pain.

Kaolin (4%, 0.1 ml) and carrageenan (2%. 0.1 ml) were injected into unilateral knee joint at 0 hour and the results are shown in FIG. 8A and FIG. 8B. The drugs were given subcutaneously daily starting on day 2. Paw withdrawal latency and knee circumference were measured at the various time points. Data analyses were done between drug and saline groups. * represents $P<0.05$,  $P<0.01$ and * $P<0.001$ compared with control (saline) in FIG. 8A, and $P<0.05-0.001$ after D5 compared to saline group in FIG. 8B. There are significant difference between combination treatment and saline groups after D3 in FIG. 8A. There are significant difference between combination treatment and saline groups after D5 in FIG. 8B.

Conclusion: Systemic injection of ketanserin and propranolol produces significant inhibition on the nociceptive threshold in the arthritic paw and edema in the arthritic joint without tolerance.

Figure 9:
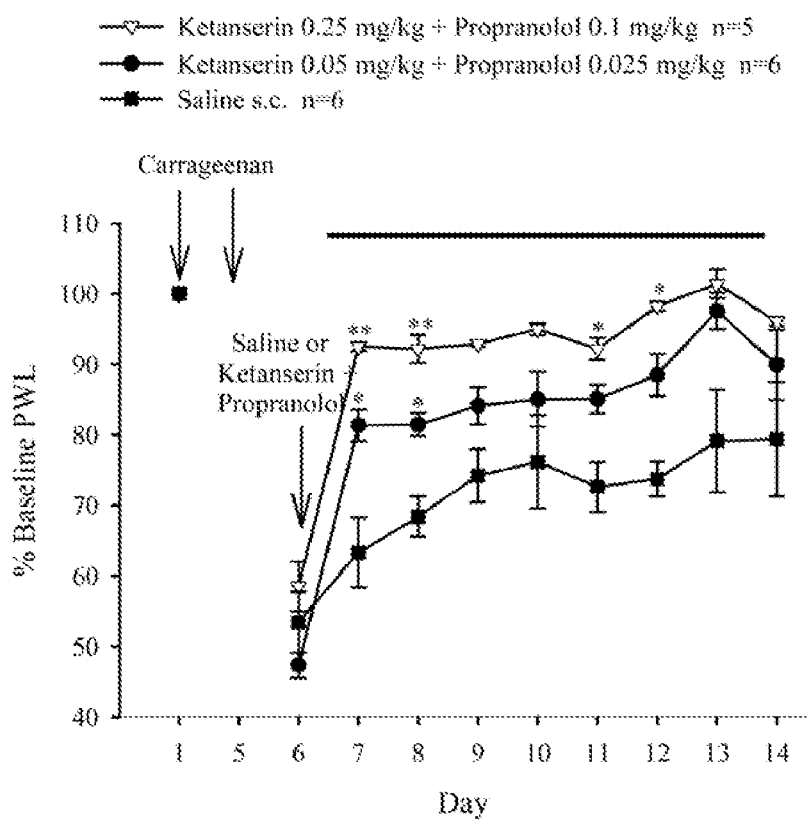
FIG. 9 shows the effects of combination of ketanserin plus propranolol on pain in a model of muscleskeletal syndrome.

Result II-4 Effects of subcutaneous injection of combination in musculoskeletal pain model (FIG. 9).

Carrageenan (3%, 0.1 ml) was injected intramuscularly in the left gastrocnemius muscle belly at days 1 and 5. Then the drugs (ketanserin plus propranolol) or saline were given subcutaneously daily starting at day 6. Paw withdrawal latency (plantar test) was measured * represents $P<0.05$ and ** $P<0.01$ and compared with control (saline).

Conclusion: Systemic injection of low doses of ketanserin+propranolol produces significant inhibition on the nociceptive threshold in the musculoskeletal pain model without tolerance.

Result II-5 Effects of subcutaneous ketanserin on thermal threshold of the hindpaw in neuropathic pain (SNL stands for spinal nerve ligation).

Figure 10:
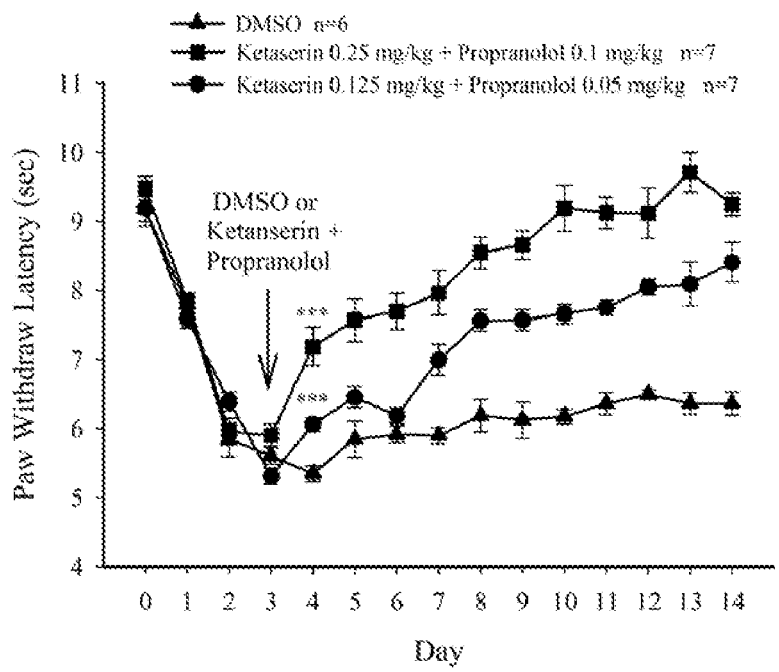
FIG. 10 shows the effects of combination of ketanserin plus propranolol on thermal hyperalgesia in a model of neuropathis pain.

Spinal nerve (L4) was ligated at day 0 and the drug or saline was injected subcutaneously starting at day 4 (FIG. 10). Paw withdrawal latency was measured.

Conclusion: Systemic injection of ketanserin dose-dependently inhibits thermal nociceptive threshold in the Chung's model of neuropathic pain without tolerance.

Result II-6 Effects of subcutaneous combination on mechanical threshold of the hindpaw in neuropathic pain (SNL)

Figure 11:
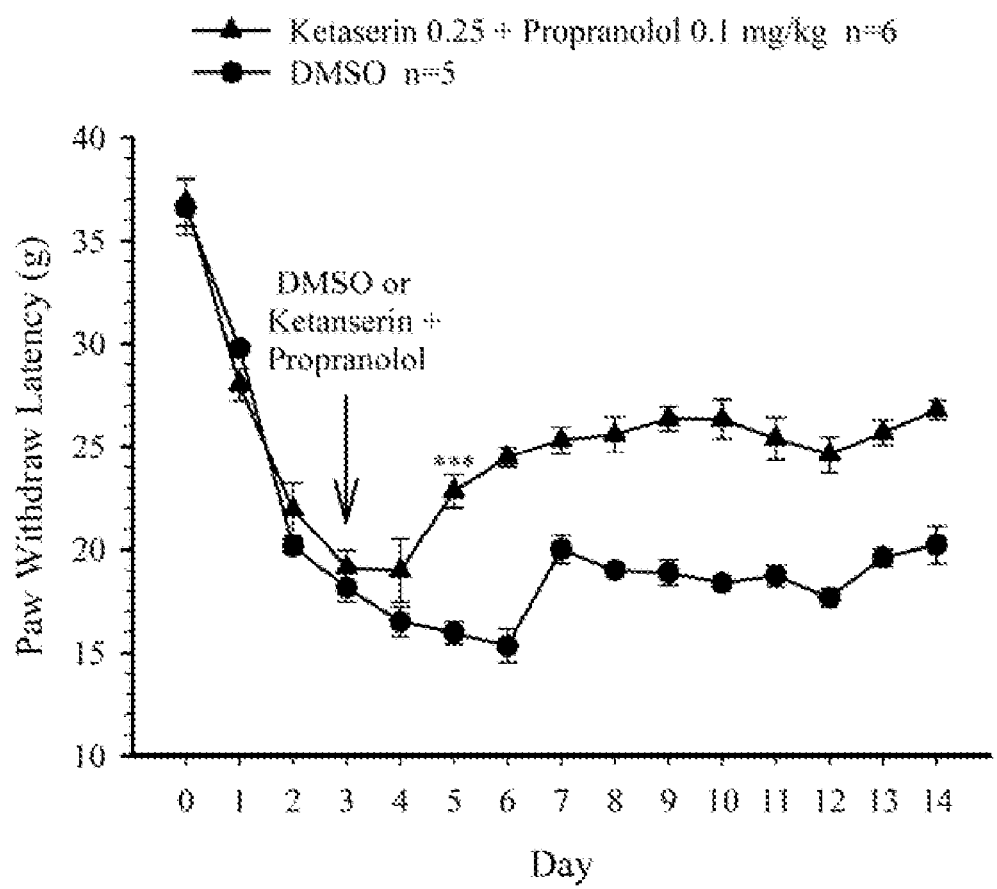
FIG. 11 shows the effects of combination of ketanserin plus propranolol on mechanical allodynia in a model of neuropathis pain.

Spinal nerve (L4) was ligated at day 0 and the drug or saline was injected subcutaneously starting at day 4 (FIG. 11). Then the drugs (ketanserin plus propranolol) or saline were given subcutaneously daily starting at day 6. Paw withdrawal latency responding to electronic von Frey monofilaments (Dynamic plantar Aesthesiometer 37400, Up Basile, Italy) was measured.

Conclusion: Systemic injection of low doses of ketanserin+propranolol produces significant inhibition on the mechanical nociceptive threshold in neuropathic pain (Chung's model) without tolerance.

Concluding Remarks

This invention proposes to locally or systemically (subcutaneously) inject a combination of ketanserin (5-$HT_{2A}$ receptor antagonist) and propranolol (5-$HT_{1A}$ receptor antagonist) to treat pain that is associated with inflammation and tissue injury.

Our study has showed that post-treatment with intraplantar ketanserin and propranolol in the inflamed site results in prolonging in paw withdrawal latency 24 hours after intraplantar injection of carrageenan. Interestingly, PWL at this time was even significantly longer than the baseline level indicating that the blockade of peripheral 5-$HT_{2A}$ or 5-$HT_{1A}$ receptors produced hypoalgesia 24 hours after inflammation. This hypoalgesia was abolished by i.p. naloxone. This is a novel discovery showing that the blockade of 5-$HT_{2A}$ or 5-$HT_{1A}$ receptor in the inflamed site inhibits activation of nociceptor and enhances endogenous opioid analgesia.

The advantage of this invention is to target peripheral receptors which play a pivotal role in mediating nociceptive responses. Therefore, the side-effects can be avoided. The excellence and novelty of the present invention is that targeting 5-$HT_{2A}$ and 5-$HT_{1A}$ at the same time produces a synergistic effects for inhibition of nociception. The $5\text{-}HT_{2A}$ and $5\text{-}HT_{1A}$ receptors that the combination of ketanserin and propranolol acts on have not been taken as targets by the existing analgesics. Importantly, the combination of these two drugs produces satisfied antinociception at low doses. Therefore, the possible side-effects can be minimal, if not zero. In addition, the analgesia occurs rapidly and lacks tolerance. Moreover, both local and systemic injections of the combination are effective. Therefore, it is convenient to use. Potential applications include arthritis, muscleskeletal pain syndrome and general inflammatory pain.

What is claimed is:

1. A combination of a mixture of 50-70% by weight of ketanserin and 50%-30% by weight of propranolol, wherein the combination is dissolved in 1 mL of water to make an injectable drug comprising 1-50 mg of the combination.

2. The combination of claim 1 is used to treat pain selected from arthritic pain, muscle skeletal pain, inflammatory pain, neuropathic pain and cancer pain.

* * * * *